United States Patent
Hattori (10) Patent No.: US 7,043,957 B2
(45) Date of Patent: May 16, 2006

(54) ELEMENT IMPEDANCE DETECTION APPARATUS AND METHOD FOR OXYGEN SENSOR

(75) Inventor: Kazutaka Hattori, Okazaki (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 244 days.

(21) Appl. No.: 10/703,451

(22) Filed: Nov. 10, 2003

(65) Prior Publication Data

US 2004/0099041 A1 May 27, 2004

(30) Foreign Application Priority Data

Nov. 25, 2002 (JP) ............... 2002-341326

(51) Int. Cl.
*G01N 21/00* (2006.01)

(52) U.S. Cl. ....................................... 73/1.06
(58) Field of Classification Search ................. 73/1.06, 73/118.1, 23.32; 204/424
See application file for complete search history.

(56) References Cited

U.S. PATENT DOCUMENTS 6,084,418 A * 7/2000 Takami et al. ............... 324/717
6,578,563 B1 * 6/2003 Hada et al. .................. 123/697

FOREIGN PATENT DOCUMENTS

| DE | 199 25 325 A1 | 12/2000 |
| JP | A 2000-28575 | 1/2000 |
| JP | A 2000-258387 | 9/2000 |

* cited by examiner

*Primary Examiner*—Robert Raevis
(74) *Attorney, Agent, or Firm*—Oliff & Berridge, PLC (57) ABSTRACT

An element impedance detection apparatus for an oxygen sensor is provided with a first switching device, a second resistor, first resistor, and a first condenser for application of a sweep voltage to the oxygen sensor. The first switching device is switched to ON and the sweep voltage applied; a sensor current I that flows in the oxygen sensor along with application of the sweep voltage is then detected. Element impedance is calculated based on the sweep voltage and the sensor current. The second resistor, the first resistor and the first condenser are connected to the oxygen sensor such that a time constant of the sweep voltage increases as the element impedance becomes larger.

12 Claims, 7 Drawing Sheets

ELEMENT IMPEDANCE DETECTION APPARATUS AND METHOD FOR OXYGEN SENSOR

INCORPORATION BY REFERENCE

The disclosure of Japanese Patent Application No. 2002-341326 filed on Dec. 25, 2002 including the specification, drawings and abstract is incorporated herein by reference in its entirety.

BACKGROUND OF THE INVENTION

1. Field of the Invention

The invention relates to an element impedance detection apparatus and method for an oxygen sensor. More particularly, the invention relates to an element impedance detection apparatus and method which is applicable to an oxygen sensor having an element impedance that changes depending on temperature characteristics, and which is suitable for measurement of an element impedance thereof.

2. Description of the Related Art

Apparatuses are known that detect element impedance of an oxygen sensor, as disclosed, for example, in Japanese Patent Laid-Open Publication No. 2000-028575. In the disclosed apparatus, a constant impressed voltage V0 is applied to the oxygen sensor; when element impedance is detected, a function of the apparatus changes the impressed voltage V0 from a reference voltage to a sweep voltage. When the impressed voltage V0 changes by a voltage change ΔV0, a current I flowing in the oxygen sensor changes by current change ΔI, which corresponds with an element impedance Rs. It should be noted that in the above-described apparatus, the element impedance of the oxygen sensor is calculated based on the voltage change ΔV0 generated by changing the impressed voltage V0 to the sweep voltage and the current change ΔI.

The apparatus described above is configured such that, when the impressed voltage V0 is changed from the reference voltage to the sweep voltage, a time constant of the change is normally constant. Further, in this apparatus, normally, both terminal voltages of the oxygen sensor are changed to the sweep voltage when element impedance is measured, regardless of the magnitude of element impedance.

Generally, element impedance of an oxygen sensor exhibits temperature characteristics, and the element impedance value changes within a substantial range. In the above-described apparatus, when element impedance becomes a sufficiently large value, even if both terminal voltages of the oxygen sensor are changed to the sweep voltage, the current I flowing in the oxygen sensor does not become excessive. However, with the above-described apparatus, in a state where element impedance is sufficiently small, when the impressed voltage V0 applied to the oxygen sensor is changed to the sweep voltage, the current I flowing in the oxygen sensor sometimes becomes excessive. In this way, a characteristic feature of the above-described apparatus is that excessive electric power is supplied to the oxygen sensor when detecting element impedance.

SUMMARY OF THE INVENTION

An object of the invention is to provide an element impedance detection apparatus and method for an oxygen sensor that can measure element impedance whilst inhibiting excessive electric power from being supplied to the oxygen sensor, even if a value of the element impedance changes.

According to a first aspect of the invention, an element impedance detection apparatus for an oxygen sensor, includes: a sweep voltage application device that applies a sweep voltage to the oxygen sensor; a sensor current detection device that detects a sensor current flowing in the oxygen sensor accompanying application of the sweep voltage; an element impedance calculation device that calculates an element impedance of the oxygen sensor, based on the sweep voltage and the sensor current; and a sweep time constant changing device that increases a time constant of the sweep voltage as the element impedance becomes larger.

According to the first aspect, at the same time as applying the sweep voltage to the oxygen sensor, it is possible to calculate the element impedance based on the current flowing in the oxygen sensor when the sweep voltage is being applied. In addition, as the element impedance becomes larger, the time constant of the sweep voltage is set to increase such that the rise of the sweep voltage is more gradual. Accordingly, it is easily possible to inhibit excessive voltage from being applied to both terminals of the oxygen sensor when the element impedance is large.

According to the first aspect of the invention, the sweep voltage application device may include a sweep voltage convergence value changing device that sets a convergence value of the sweep voltage to become smaller as the element impedance becomes larger. As a result of this configuration, as the element impedance becomes larger, it is possible to set the convergence value of the sweep voltage applied to the oxygen sensor to become smaller. Accordingly, when the element impedance is small, and a large current flows in the oxygen sensor, it is possible to effectively inhibit the supply of electric power to the oxygen sensor from becoming excessive by setting the applied voltage (the sweep voltage) to a small value.

According to the above aspect, the sweep voltage application device may include a constant voltage generation device that generates a constant voltage when connected in series with the oxygen sensor; and a resistor that is arranged between the oxygen sensor and the constant voltage generation device. In addition, the sweep voltage convergence value changing device may include the oxygen sensor and the resistor. As a result of this configuration, by arranging the power source generating the constant voltage, the resistor, and the oxygen sensor in series, it is possible to easily realize a function that makes the convergence value of the sweep voltage smaller as the element impedance of the oxygen sensor becomes smaller.

According to the first aspect of the invention may also include a sweep voltage application interruption device that interrupts application of the sweep voltage at a time point when a predetermined application period has elapsed after application of the sweep voltage to the oxygen sensor starts. Moreover, the application period may be set to a period that is necessary for the sweep voltage for the element impedance to converge on the convergence value when the oxygen sensor is being operated under normal conditions. As a result of this configuration, it is possible to interrupt application of the sweep voltage at the time point when the period necessary for the sweep voltage for the element impedance to converge on the convergence value has elapsed when the oxygen sensor is operating under normal usage conditions. As a result, when the element impedance is large, the sweep voltage is interrupted prior to when the sweep voltage reaches the convergence value, and thus it is possible to inhibit the electric power supplied to the oxygen sensor from becoming excessive.

According to the first aspect, the sweep voltage application device may include a constant voltage generation device that generates a constant voltage when connected in series with the oxygen sensor, and a condenser which is connected in series with the constant voltage generation device and which is connected in parallel with the oxygen sensor. Further, the sweep time constant changing device may switch the time constant in accordance with a capacity of the condenser. As a result of this configuration, an RC circuit is configured by the oxygen sensor itself and the condenser connected in parallel with it. Moreover, it is possible to supply constant voltage to the RC circuit during the application period of the sweep voltage. Given this, it is possible to satisfy the requirement that the time constant is set to increase as the element impedance becomes larger, due to the characteristics of the RC circuit.

According to the first aspect, the sweep voltage application device may include a time constant changing device that switches the time constant for the single element impedance between, at the least, two of the time constant. Moreover, the element impedance calculation device includes an element impedance ratio calculation device that calculates the element impedance of the oxygen sensor with respect to the, at the least, two time constants, and derives a ratio of the element impedances calculated with respect to each of, at the least, two of the time constant. In addition, the element impedance calculation device may include a deterioration diagnosis device that executes deterioration diagnosis for the oxygen sensor based on the element impedance ratio. As a result of this configuration, it is possible to apply the sweep voltage using, at the least, two of time constant for each element impedance. Moreover, it is possible to execute the deterioration diagnosis for the oxygen sensor based on the ratio of the element impedances calculated with respect to each of the time constants. By adopting this method, it is possible to precisely execute deterioration detection for the oxygen sensor without the temperature characteristics of the element impedance having any affect.

According to the above aspect, the sweep voltage application device may include a constant voltage generation device which generates a constant voltage when connected in series with the oxygen sensor, and a variable capacity condenser which is connected in series with the constant voltage generation device and which is connected in parallel with the oxygen sensor. Moreover, the time constant changing device may include a capacity changing device that changes a capacity of the variable capacity condenser. As a result of this configuration, it is possible to easily switch the time constant of the sweep voltage by changing the capacity of the variable capacity condenser connected in parallel with the oxygen sensor.

According to a second aspect of the invention, an element impedance detection apparatus for an oxygen sensor, includes; sweep voltage application means that applies a sweep voltage to the oxygen sensor; sensor current detection means that detects a sensor current flowing in the oxygen sensor accompanying application of the sweep voltage; element impedance calculation means that calculates an element impedance of the oxygen sensor, based on the sweep voltage and the sensor current; and sweep time constant changing means that sets a time constant of the sweep voltage to increase as the element impedance becomes larger. As a result of this configuration, at the same time as applying the sweep voltage to the oxygen sensor, it is possible to calculate the element impedance based on the current flowing in the oxygen sensor when the sweep voltage is being applied. In addition, as the element impedance becomes larger, the time constant of the sweep voltage is set to increase such that the rise of the sweep voltage is more gradual. Accordingly, it is easily possible to inhibit excessive voltage from being applied to both terminals of the oxygen sensor when the element impedance is large.

According to a third aspect of the invention, an element impedance detection method for an oxygen sensor includes the steps of: applying a sweep voltage to the oxygen sensor in accordance with a time constant of the sweep voltage; detecting a sensor current flowing in the oxygen sensor accompanying application of the sweep voltage; calculating an element impedance of the oxygen sensor based on the sweep voltage and the sensor current; and switching the time constant such that the time constant of the sweep voltage increases as the element impedance becomes larger. As a result of adopting this method, at the same time as applying the sweep voltage to the oxygen sensor, it is possible to calculate the element impedance based on the current flowing in the oxygen sensor when the sweep voltage is being applied. In addition, as the element impedance becomes larger, the time constant of the sweep voltage is set to increase such that the rise of the sweep voltage is more gradual. Accordingly, it is easily possible to inhibit excessive voltage from being applied to both terminals of the oxygen sensor when the element impedance is large.

According to the third aspect, the step of applying the sweep voltage may include a step of changing a convergence value of the sweep voltage such that the convergence value becomes smaller as the element impedance becomes larger. As a result of adopting this method, as the element impedance becomes larger, it is possible to set the convergence value of the sweep voltage applied to the oxygen sensor to become smaller. Accordingly, when the element impedance is small, and a large current flows in the oxygen sensor, it is possible to effectively inhibit the supply of the electric power to the oxygen sensor from becoming excessive by setting the applied voltage (the sweep voltage) to a small value.

According to the third aspect, the element impedance detection method may further include the step of interrupting application of the sweep voltage at a time point when a predetermined application period has elapsed after application of the sweep voltage to the oxygen sensor starts. Further, the predetermined application period may be set to a period that is necessary for the sweep voltage for the element impedance to converge on the convergence value when the oxygen sensor is being operated under normal conditions. As a result of adopting this method, it is possible to interrupt application of the sweep voltage at the time point when the period necessary for the sweep voltage for the element impedance to converge on the convergence value has elapsed when the oxygen sensor is operating under normal usage conditions. As a result, when the element impedance is large, the sweep voltage is interrupted prior to when the sweep voltage reaches the convergence value, and thus it is possible to inhibit the electric power supplied to the oxygen sensor from becoming excessive.

According to the third aspect, the step of applying the sweep voltage may include the step of switching the time constant for the single element impedance between, at the least, two of the time constant. Moreover, the step of calculating the element impedance may include the step of deriving a ratio of the element impedances calculated with respect to each of, at the least, two of the time constant by calculating the respective element impedances of the oxygen sensor with respect to, at the least, two of the time constant. In addition, the step of calculating the element impedance may also include the step of executing deterioration diagnosis for the oxygen sensor based on the element impedance ratio. As a result of adopting this method, it is possible to apply the sweep voltage using, at the least, two of the time constant for the single element impedance. Moreover, it is possible to execute the deterioration diagnosis for the oxygen sensor based on the ratio of the element impedances calculated with respect to each of the time constants. By utilizing this method, it is possible to precisely execute deterioration detection for the oxygen sensor without the temperature characteristics of the element impedance having any affect.

BRIEF DESCRIPTION OF THE DRAWINGS

The foregoing and further objects, features and advantages of the invention will become apparent from the following description of preferred embodiments with reference to the accompanying drawings, wherein like numerals are used to represent like elements and wherein:

FIG. 4A to FIG. 4D are timing charts that illustrate an operation that is realized each time the apparatus of the embodiment switches a first port 24 to ON;

DETAILED DESCRIPTION OF THE PREFERRED EMBODIMENTS

Hereinafter, a preferred embodiment of the invention will be explained with reference to the drawings. It should be noted that elements that are the same in each drawing are denoted by the same reference numerals, and repeated explanation is omitted.

Figure 1:
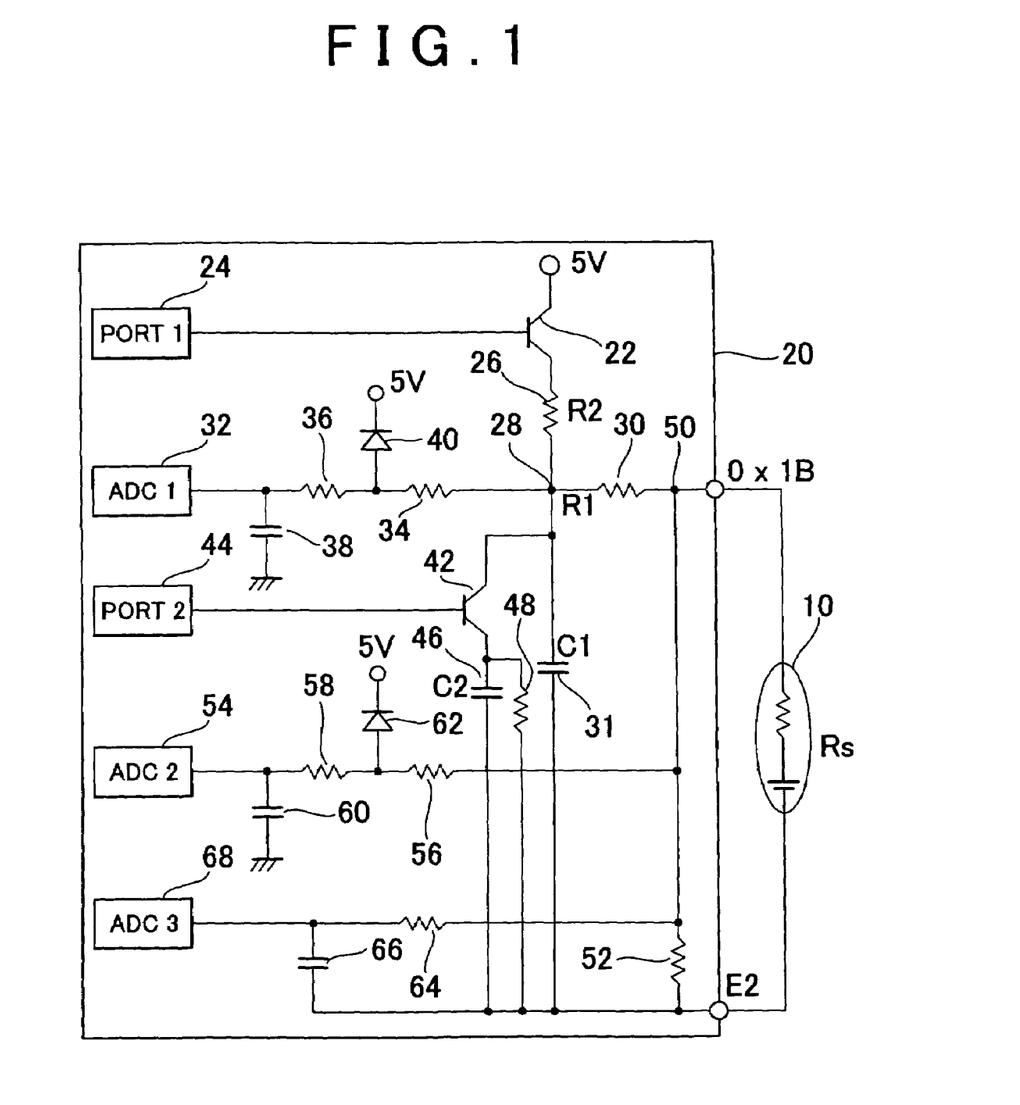
FIG. 1 is an explanatory figure of a configuration of an embodiment of the invention.

FIG. 1 is an explanatory figure of a configuration of an embodiment of the invention. As shown by FIG. 1, a system of the embodiment is provided with an oxygen sensor 10 and an electronic control unit (ECU) 20. The oxygen sensor 10 may be, for example, disposed in an exhaust passage of an internal combustion engine, and can be used to detect an oxygen concentration within exhaust gas.

In FIG. 1, the oxygen sensor 10 is configured by including an impedance component and an electromotive force component. In other words, the oxygen sensor 10 is an electromotive force type sensor that generates voltage in accordance with an oxygen concentration within a detected gas. In the embodiment, the oxygen sensor 10 and the ECU 20 are connected such that an external connection terminal 0X1B side is the high voltage side and an external connection terminal E2 side is the low voltage side.

An element impedance Rs of the oxygen sensor 10 exhibits temperature characteristics. The value of the element impedance Rs becomes smaller as the temperature increases. In order for the oxygen sensor 10 to function normally, it is necessary to control the temperature of the oxygen sensor 10 to an activation temperature. Since the temperature of the oxygen sensor 10 has a correlation with the element impedance Rs, it is beneficial from the point of view of controlling the temperature to the activation temperature if the element impedance Rs can be accurately detected. Moreover, if the element impedance Rs is accurately detected, it is possible to execute abnormality diagnosis for the oxygen sensor 10 based on the detected value. Given these considerations, accurate detection of the element impedance Rs is a requirement for the oxygen sensor 10.

In response to this requirement, the ECU 20 is configured so as to precisely detect the element impedance Rs of the oxygen sensor 10. Hereinafter, a circuit configuration and functions of the ECU 20 will be described in detail.

The ECU 20 is provided with a first switching element 22. A constant voltage (power source voltage) of 5V is supplied to the first switching device 22. A gate of the first switching device 22 is connected to a first port 24. The ECU 20, when necessary, switches the first switching device 22 to ON by outputting an ON command to the first port 24.

A second resistor 26 is connected in series with the first switching device 22. The second resistor 26 is also connected to a first sampling point 28. The first sampling point 28 is connected to the external connection terminal 0X1B of the ECU 20 via a first resistor 30, and is also connected to the external connection terminal E2 of the ECU 20 via a first condenser 31. In other words, a series circuit including the first resistor 30 and the oxygen sensor 10 is connected to the first sampling point 28, and furthermore, the first condenser 31, which is connected in parallel with the series circuit, is also connected to the first sampling point 28.

The first sampling point 28 is connected to a first AD converter (ADC1) 32 via a first filter circuit with a short time constant. The first filter circuit is provided with two resistors 34 and 36 connected in series, and a condenser 38 arranged between an input terminal of the first AD converter 32 and a ground wire. A diode 40 is connected between the two resistors 34 and 36 in order to maintain an electric potential at the connection point of the resistors 34 and 36 at equal to or less than 5V.

The first AD converter 32 can convert an analogue signal that is input to the input terminal into a digital signal; the digital signal is then output. An electric potential of the first sampling point 28 is applied to the input terminal of the first AD converter 32 via the previously described first filter circuit with the short time constant. Accordingly, the first AD converter 32 can precisely digitize and output the electric potential of the first sampling point 28, even when the electric potential changes at high frequency. As will be described later, under certain conditions, the ECU 20 recognizes the digital signal output by the first AD converter 32 as the electric potential of the first sampling point 28, and utilizes the digital signal in detection processing of the element impedance Rs.

One end of the first condenser 31 is connected to the first sampling point 28. The other end of the first condenser 31 is connected to the external connection terminal E2 of the ECU 20. Accordingly, the first sampling point 28 is connected to the oxygen sensor 10 via the first condenser 31.

Further, a second switching device 42 is connected to the first sampling point 28. A second port 44 is connected to a gate of the second switching device 42. The ECU 20, when necessary, switches the second switching device 42 to ON by outputting an ON command to the second port 44.

In addition, one end of a second condenser 46 is connected to the second switching device 42. The other end of the second condenser 46 is connected to the external connecting terminal E2. In other words, in this circuit, the second switching device 42 and the second condenser 46 connected in series are arranged between the first sampling point 28 and the external connecting terminal E2 in parallel to the first condenser 31. Accordingly, the ECU 20 is able to configure the circuit such that the oxygen sensor 10 and the first condenser 31 are connected in parallel when the second port 44 outputs an OFF command. Further, when the second port 44 outputs an ON command, the ECU 20 is able to configure the circuit such that a parallel combined condenser, which is formed by parallel connection of the first condenser 31 and the second condenser 46, is connected in parallel with the oxygen sensor 10.

The second condenser 46 has a capacity that is around one hundred times the size of a capacity of the first condenser 31. Accordingly, when the second condenser is connected in parallel with the first condenser 31, the above-described parallel combined condenser is formed which has the capacity that is over one hundred times the size of the capacity of the first condenser 31. As a result, the ECU 20 is able to change the capacity of the condenser connected in parallel to the oxygen sensor 10 within a range of around one hundred times.

Note that, in the ECU 20, when the second switching device 42 is ON a load flows to the second condenser 46. This load must be discharged once the second switching device 42 is switched to OFF. Accordingly, a discharge resistor 48 is connected in parallel with the second condenser 46.

In the ECU 20, a second sampling point 50 is formed between the first resistor 30 and the external connection terminal 0X1B. One end of an output detection resistor 52 arranged in parallel with the oxygen sensor 10 is connected to the second sampling point 50. The output detection resistor 52 has as impedance that is sufficiently larger, as compared to the element impedance Rs of the oxygen sensor 10. Accordingly, when the voltage of the power source is not supplied to the second sampling point 50 (when the first switching device 22 is OFF), a voltage is generated at the second sampling point 50 that corresponds to the electromotive-force of the oxygen sensor 10. Further, when the voltage of the power source is supplied to the second sampling point 50 (when the first switching device 22 is ON), a voltage is generated at the second sampling point 50 that corresponds to the product of the current I flowing in the oxygen sensor 10 and the element impedance Rs.

The second sampling point 50 is connected to a second AD converter (ADC2) 54 via a second filter circuit with a short time constant. The second filter circuit is provided with two resistors 56 and 58 connected in series, and a condenser 60 arranged between an input terminal of the second AD converter 54 and a ground wire. A diode 62 is connected between the two resistors 56 and 58 in order to maintain an electric potential at the connection point of the resistors 56 and 58 at equal to or less than 5V.

The second AD converter 54 can convert an analogue signal that is input to the input terminal into a digital signal; this digital signal is then output. The second sampling point 50 is connected to the input terminal of the second AD converter 54 via the previously described second filter circuit with the short time constant. Accordingly, the second AD converter 54 can precisely digitize and output an electric potential of the second sampling point 50, even when this electric potential changes at high frequency. As will be described later, under certain conditions, the ECU 20 recognizes the digital signal output by the second AD converter 54 as the electric potential of the second sampling point 50, and utilizes the digital signal in detection processing of the element impedance Rs.

In addition, a third 3AD converter (ADC3) 68 is connected to the second sampling point 50 via a third filter circuit formed from a resistor 64 and a condenser 66. The third filter circuit, which is provided upstream in the circuit from the third 3AD converter 68, has a time constant that is sufficiently large; thus, the third filter circuit only allows low frequency components of the voltage of the second sampling point 50 to pass. Accordingly, the third 3AD converter 68 is not subject to the influence of noise, and the like, and it is possible to generate a precise digital signal that corresponds with the normal voltage value of the second sampling point 50. As will be described later, under certain conditions, the ECU 20 recognizes the digital signal output by the third 3AD converter 68 as the output signal of the oxygen sensor 10, and utilizes the digital signal in detection processing of the oxygen concentration within the detected gas.

Figure 2:
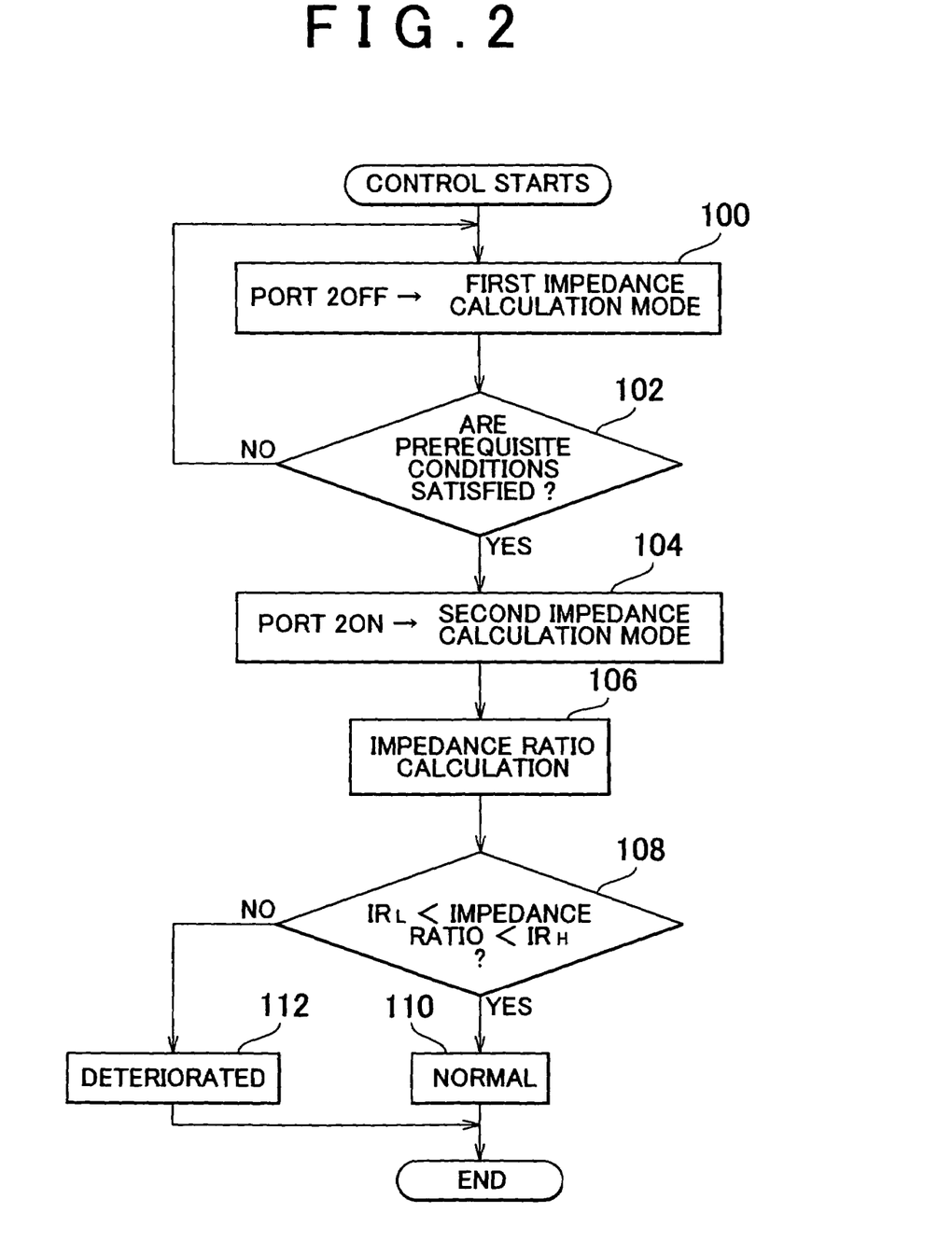
FIG. 2 is a flow chart that illustrates an overall flow of a control executed by the embodiment of the invention.

Next, an overall flow of a control executed by the ECU 20 will be explained with reference to FIG. 2. FIG. 2 is a flowchart that illustrates the overall flow of the control executed by the ECU 20 in the embodiment. This control determines whether or not the oxygen sensor 10 is functioning normally based on a result obtained from detection of the element impedance Rs of the oxygen sensor 10.

In the embodiment, the oxygen sensor 10 is disposed within the exhaust passage of the internal combustion engine. Accordingly, the oxygen sensor 10 is warmed up by exhaust gas heat following starting of the internal combustion engine. The ECU 20 executes processing in order to estimate the temperature of the oxygen sensor 10; this processing is separate from the control shown in FIG. 2. In this processing, for example, the temperature of the oxygen sensor 10 is estimate based on an integrated value of an intake air amount that has been intaken following starting of the internal combustion engine. More specifically, the temperature is estimated based on an integrated amount of the exhaust gas discharged from the internal combustion engine.

The control shown in FIG. 2 is initiated once the temperature estimated in this manner exceeds a predetermined activation temperature (for example, 350° C.). The element impedance Rs of the oxygen sensor 10 exhibits the same temperature characteristics as previously described. The element impedance Rs becomes several tens of kΩ or less when the temperature of the oxygen sensor 10 is in a temperature region that is greater than the activation temperature. Accordingly, execution of the control shown in FIG. 2 is limited to those times when the element impedance Rs is several tens of kΩ or less.

In the routine shown in FIG. 2, first, while the second port 44 is OFF, processing in a first impedance calculation mode is executed (step S100). In the first impedance calculation mode, normally, the second switching device 42 is maintained in the OFF position. In this case, the circuit configuration within the ECU 20 is such that the oxygen sensor 10 is connected in parallel with the condenser 31. The first impedance calculation mode is a mode that, under these conditions, detects the element impedance Rs while detecting the sensor output of the oxygen sensor 10. Hereinafter, the element impedance Rs detected in the mode will be referred to as "first impedance Rs1". It should be noted that further details of the specific processing executed in the first impedance calculation mode will be described later with reference to FIGS. 4A to 4D and FIG. 5.

In the routine shown in FIG. 2, following completion of the processing of the first impedance calculation mode, it is determined whether prerequisite conditions for executing a second impedance calculation mode are satisfied (step S102). More particularly, in step 102, it is determined whether the temperature of the oxygen sensor 10 exceeds an execution temperature (for example, 500° C.) for the second impedance calculation mode.

In the case that the result of the previously described determination is that the prerequisite conditions are satisfied, next, the second port 44 is switched to ON, and processing of the second impedance calculation mode is executed (step S104). In the second impedance calculation mode, normally, the second switching device 42 is maintained in the ON position. In this case, the circuit configuration within the ECU 20 is such that the oxygen sensor 10 is connected in parallel with the condenser 31 as well as the condenser 46. The second impedance calculation mode is a mode that, under these conditions, detects the element impedance Rs while detecting the sensor output of the oxygen sensor 10. Hereinafter, the element impedance Rs detected in the mode will be referred to as "second impedance Rs2". It should be noted that further details of the specific processing executed in the first impedance calculation mode will be described later with reference to FIGS. 4A to 4D and FIG. 5.

Next, in the routine shown in FIG. 2, an impedance ratio that equals Rs1/Rs2, is calculated (step S106).

According to the above described first impedance calculation mode it is possible to detect the element impedance Rs while applying the sweep voltage changed at the short time constant, namely, a sweep voltage that rises rapidly, to the oxygen sensor 10 (the reason for this will be explained later). Accordingly, the first impedance Rs1 is the element impedance Rs that is exhibited when both terminal voltages of the oxygen sensor 10 change at a high frequency.

On the other hand, in the above described second impedance calculation mode it is possible to detect the element impedance Rs while applying the sweep voltage changed at the long time constant, namely, a sweep voltage that rises gradually, to the oxygen sensor 10 (the reason for this will be explained later). Accordingly, the second impedance Rs2 is the element impedance Rs that is exhibited when both terminal voltages of the oxygen sensor 10 change at a low frequency.

The element impedance Rs of the oxygen sensor 10 does not have frequency characteristics during an initial period of usage of the oxygen sensor 10 when it is new. Accordingly, during the initial period, the impedance ratio Rs1/Rs2 is substantially equal to 1. However, the element impedance of the oxygen sensor 10 begins to exhibit frequency characteristics along with the progression of deterioration of the oxygen sensor 10 (generally, the element impedance Rs at low frequency becomes a higher value). As a result, the impedance ratio Rs1/Rs2 is a value that moves further away from 1 along with the progression of deterioration of the oxygen sensor 10.

In the routine shown in FIG. 2, following the processing of step S106, it is determined (step S108) whether the impedance ratio Rs1/Rs2 is larger than a lower limit determination value $IR_L$ (for example, 0.8), and smaller than an upper limit determination value $IR_H$ (for example, 1.2).

When the result is that $IR_L 20 < Rs1/Rs2 < IR_H$ is satisfied, it is determined that the oxygen sensor is functioning normally (step S110); on the other hand, when this is not satisfied, it is determined that the oxygen sensor 10 has deteriorated (step S112).

[Detailed Explanation of the Control Executed by ECU]

Next, the specific details of the processing executed in the first impedance calculation mode and the second impedance calculation mode will be explained with reference to FIGS. 3A and 3B, and FIGS. 4A to 4D.

Figure 3A:
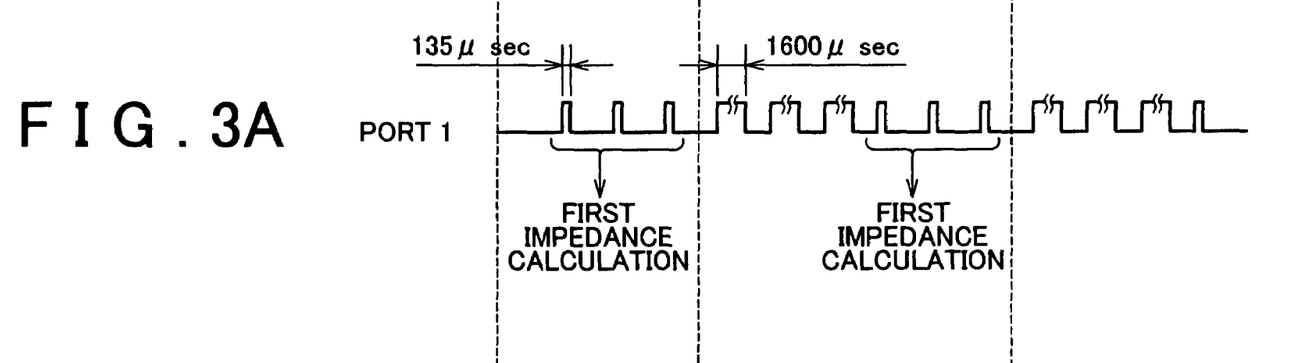
FIG. 3A and FIG. 3B are timing charts that illustrate an overall flow of a control executed by an apparatus of the embodiment of the invention.
Figure 3B:
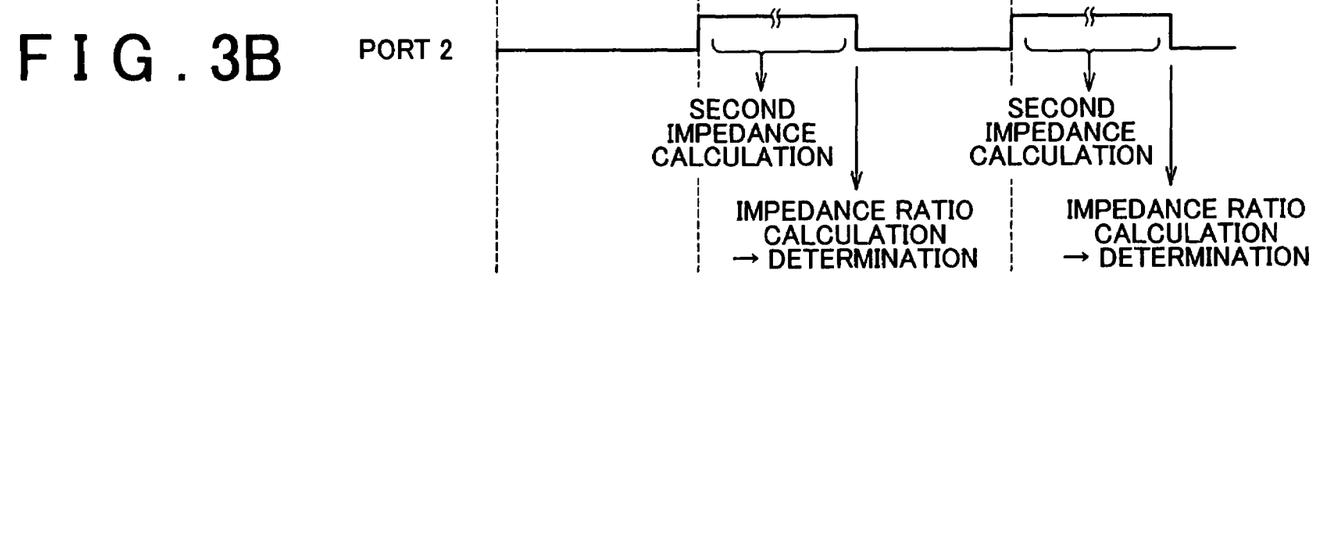

FIGS. 3A and 3B are timing charts that illustrate an operation realized by the ECU 20 executing processing in accordance with the flow chart shown in FIG. 2. More specifically, FIG. 3A is a timing chart showing the ON/OFF position of the first port 24, and FIG. 3B is a timing chart showing the ON/OFF position of the second port 44.

In the example shown in FIGS. 3A and 3B, in the first impedance calculation mode and the second impedance calculation mode, the first port 24 is respectively switched to the ON position three times. On these occasions, in the first impedance calculation mode, the first port 24 is maintained in the ON position for a period of 135 μsec for each time the first port 24 is switched to ON. Moreover, in the second impedance calculation mode, the first port 24 is maintained in the ON position for a period of time that is about 10 times the ON period of the first impedance calculation mode (for example, 1600 μsec), for each time the first port 24 is switched to ON.

The first impedance Rs1 and the second impedance Rs2 are calculated each time the first port 24 is switched to ON in the respective modes. When the respective modes are terminated, the ECU 20 determines the first impedance Rs1 and the second impedance Rs2 for each cycle by respectively averaging the impedances, which have been calculated three times. Every time the pair of impedances Rs1 and Rs2 have been determined, calculation of the impedance ratio Rs1/Rs2, and an abnormality determination for the oxygen sensor 10 are both executed.

[Detection Processing of Oxygen Concentration]

As shown in FIGS. 3A and 3B, with the system of the embodiment, there is a period in both the first impedance calculation mode and the second impedance calculation mode when the first port 24 is switched to OFF. During the period in which the first port 24 is OFF, namely, during a period in which the first switching device 22 is OFF, an electric potential that corresponds to the electromotive force of the oxygen sensor 10 is generated at the second sampling point 50 (refer to FIG. 1). In this case, the output of the third 3AD converter 68 agrees with the sensor output of the oxygen sensor 10. Under these conditions, the ECU 20 detects the digital signal output by the third 3AD converter 68 at a predetermined cycle (for example, every 4 m sec), and detects the oxygen concentration within the detected gas (the exhaust gas).

[Calculation Processing of the First Impedance Rs1]

In the first impedance calculation mode the second port 44 is maintained in the OFF position. In other words, the second switching device 42 is maintained in the OFF position. In this case, the circuit configuration within the ECU 20 is such that only the first condenser 31 is connected in parallel with the in series circuit of the first resistor 30 and the oxygen sensor 10. Hereinafter, the parallel circuit formed by these elements will be referred to as "R1.Rs–C1 parallel circuit".

Figures 4A, 4B:
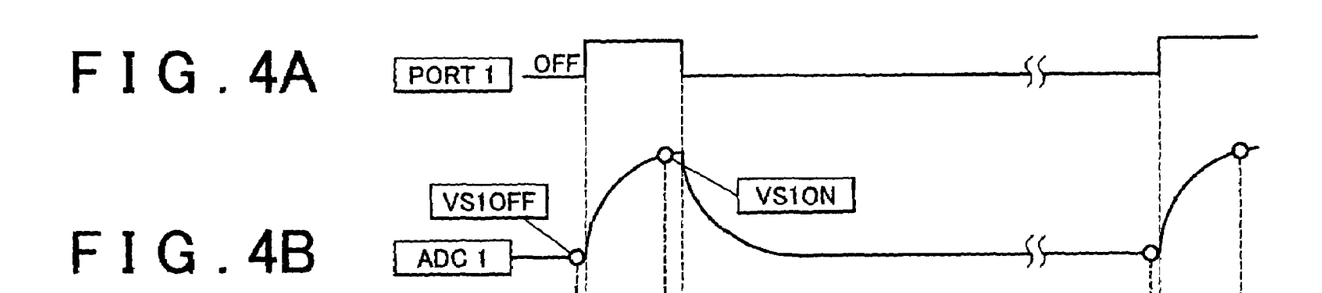
Figure 4C:
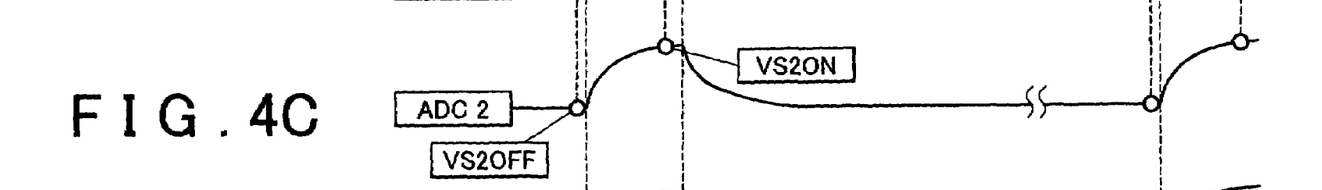
Figure 4D:
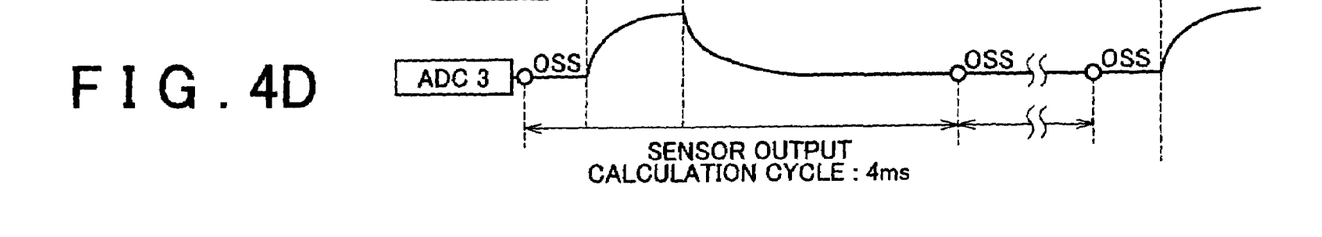

FIGS. 4A to 4D are timing charts that illustrate an operation in the case that the first port 24 is repeatedly switched to ON and OFF under the above described conditions. More particularly, FIG. 4A shows a waveform illustrating the position of the first port 24, and FIGS. 4B to 4D show waveforms illustrating changes in the electric potential applied to the respective input terminals of the first AD converter 32, the second AD converter 54, and the third 3AD converter 68.

With the circuit configuration shown in FIG. 1, when the first port 24 is ON, and the first switching device 22 is ON, the power source voltage of 5V is applied to the second resistor 26. The voltage is applied to the first sampling point 28 through the second resistor 26, and is applied to the R1.Rs–C1 parallel circuit. Note that the ECU 20 is provided with the output detection resistor 52 connected in parallel with the oxygen sensor 10. However, the resistance value is sufficiently large as compared to the resistance value of the element impedance Rs of the oxygen sensor 10 (which is several tens kΩ or less). Thus, it is possible to ignore the influence of the output detection resistor 52 at this point.

Once the voltage, as described above, starts to be applied to the first sampling point 28, an electric potential VS1 at the first sampling point 28 increases at a time constant τ1. Eventually, the electric potential VS1 converges onto a value determined by dividing a resistance value R2 of the second resistor 26, and the combined resistance values R1 and Rs of the first resistor 30 and the oxygen sensor 10. In this case, the convergence value VS1 and the time constant τ1 can be expressed using the following Equation (1) and Equation (2).

$$VS1 = 5 \cdot (R1+Rs)/(R2+R1+Rs) \quad (1)$$

$$\tau 1 = C1/\{1/(Rs+R1)+1/R2\} \quad (2)$$

In the circuit shown in FIG. 1, the electric potential VS1 at the first sampling point 28 is applied to the first AD converter 32. As a result, the output of the first AD converter 32 exhibits the same change as the convergence value VS1 expressed using Equation (1) and Equation (2) above. The waveform in FIG. 4B shows the manner in which the output value changes of the first AD converter 32 after the first port 24 has been switched to ON.

During the process in which the electric potential VS1 at the first sampling point 28 changes in the described manner, the current I, which is expressed by Equation (3) that follows, flows in the oxygen sensor 10.

$$I = VS1/(R1+Rs) \quad (3)$$

At this time, an electric potential VS2 at the second sampling point 50 can be expressed by Equation (4) below using the current I and the element impedance Rs.

$$VS2 = Rs \cdot I \quad (4)$$

Since the electric potential VS1 at the first sampling point 28 changes at the time constant τ1, the current I that satisfies the relationship of Equation (3), as well as the electric potential VS2 at the second sampling point 50 that satisfies the relationship of Equation (4), respectively change at the time constant τ1. In the circuit shown in FIG. 1, the electric potential VS2 at the second sampling point 50 is applied to the second AD converter 54. Accordingly, the output of the second AD converter 54 exhibits the same change as the electric potential VS2 expressed by Equation (4) and Equation (2). Moreover, the waveform in FIG. 4C shows the manner in which the output value changes the second AD converter 54 after the first port 24 has been switched to ON.

The current I that flows in the oxygen sensor 10 can be expressed using Equation (5) below, using the electric potential VS1 at the first sampling point 28, the electric potential VS2 at the second sampling point 50, and the resistance value R1 of the first resistor 30.

$$I = (VS1-VS2)/R1 \quad (5)$$

The element impedance Rs can be expressed using Equation (6) below, using Equation (4) and Equation (5).

$$Rs = VS2/I = VS2 \cdot R1/(VS1-VS2) \quad (6)$$

As has been described above, in the circuit of the embodiment, the element impedance Rs of the oxygen sensor 10 can be calculated based on the electric potentials VS1 and VS2 that are respectively generated at the first sampling point 28 and the second sampling point 50, after the first port 24 has been switched to ON. However, the effects of leak current and the like, generated prior to when the first port 24 was switched to ON, superimpose on the electric potential VS1 at the first sampling point 28 and the electric potential VS2 at the second sampling point 50 after the first port 24 is switched to ON. Accordingly, in order to precisely calculate the element impedance Rs, it is desirable if the effects of leak current, and the like, are excluded.

To address this, the ECU 20 derives an electric potential difference ΔVS1 between the electric potential VS1 immediately prior to when the first port 24 is switched to ON (hereinafter referred to as "VS1OFF"), and the electric potential VS1 after the first port 24 is switched to ON (hereinafter referred to as "VS1ON"). In addition, the ECU 20 derives an electric potential difference ΔVS2 between the electric potential VS2 immediately prior to when the first port 24 is switched to ON (hereinafter referred to as "VS2OFF"), and the electric potential VS2 after the first port 24 is switched to ON (hereinafter referred to as "VS2ON"). Then, the derived electric potential differences ΔVS1 and ΔVS2 are applied to Equation (6), and the element impedance Rs is calculated in accordance with Equation (7) below.

$$Rs = \Delta VS2 \cdot R1/(\Delta VS1 - \Delta VS2) = (VS2ON - VS2OFF) \cdot R1/\{(VS1OFF - VS1ON) - (VS2OFF - VS2ON)\} \quad (7)$$

However, when the effect of leak current, and the like, is small, and VS1OFF and VS2OFF are substantially equal, it is not essential to utilize the relationship expressed in Equation (7). In this case, the element impedance Rs may be calculated in accordance with Equation (6) (with VS1=VS1ON, and VS2=VS2ON).

As described previously, the ECU 20 can detect the electric potential at the first sampling point 28 using the first AD converter 32, and in addition, can detect the electric potential at the second sampling point 50 using the second AD converter 54. Accordingly, during execution of the first impedance calculation mode, more specifically, the ECU 20 calculates the element impedance Rs using the following procedure, each time the first port 24 is switched to ON.

(A1) Immediately prior to when the first port 24 is switched to ON, the output of the first AD converter 32 is detected as VS1OFF, and the output of the second AD converter 54 is detected as VS2OFF. (A2) Once the previously described detection is completed, the first port 24 is switched to ON. (A3) Once a predetermined time period (for example, 135 μsec) has elapsed after the first port 24 has been switched to ON, the output of the first AD converter 32 is detected as VS1ON, and the output of the second AD converter 54 is detected as VS2ON. (A4) Once the previously described detection is completed, the first port 24 is switched back to OFF. (A5) The element impedance Rs is calculated by substituting the VS1OFF, VS1ON, VS2OFF, and VS2ON detected by the processing of (A1) to (A3) into Equation (7).

[Calculation Processing of the Second Impedance Rs2]

In the second impedance calculation mode, the second port 44 is maintained in the ON position. In other words, the second switching device 42 is maintained in the ON position. In this case, the circuit configuration within the ECU 20 is such that both the first condenser 31 and the second condenser 46 are both connected in parallel with the in series circuit of the first resistor 30 and the oxygen sensor 10. Hereinafter, the parallel circuit formed by these elements will be referred to as "R1.Rs–C1–C2 parallel circuit".

When the first port 24 is switched to ON in the second impedance calculation mode, the voltage applied to the first sampling point 28 is applied to the R1.Rs–C1–C2 parallel circuit. In this case, the electric potential VS1 at the first sampling point 28 increases at a time constant τ2. Eventually, the electric potential VS1 of the first sampling point 28 converges onto the electric potential VS1=5·(R1+Rs)/(R2+R1+Rs) expressed by Equation (1). Moreover, in this case, the time constant τ2 can be expressed using Equation (8) below.

$$\tau2=(C1+C2)/\{1/(Rs+R1)+1/R2\} \quad (8)$$

As described previously, the second condenser 46 has the capacity C2 that is around one hundred times that of the capacity of the first condenser 31. Accordingly, the time constant τ2 is approximately one hundred times the time constant τ1 calculated by Equation (2). As a result, in the second impedance calculation mode, after the first port 24 is switched to ON, a sweep voltage that rises sufficiently slowly as compared to that of the first impedance calculation mode is applied to the oxygen sensor 10.

In the second impedance calculation mode as well, after the first port 24 is switched to ON, the relationship of Equation (6), namely, the relationship shown below, is established.

$$Rs=VS2\cdot R1/(VS1-VS2)$$

Similarly, the relationship of Equation (7), namely, the relationship shown below, is also established in the second impedance calculation mode.

$$Rs=(VS2ON-VS2OFF)\cdot R1/\{(VS1OFF-VS1ON)-(VS2OFF-VS2ON)\}$$

Accordingly, the ECU 20, during execution of the second impedance calculation mode as well, calculates the element impedance Rs based on the procedure that was used during execution of the first impedance calculation mode (the procedure (A1) to (A5) described previously). However, in the second impedance calculation mode, the time constant τ2 is set to the larger value, and the rise of the sweep voltage is gradual. Accordingly, the time for which the first port 24 is maintained in the ON position is set to about 10 times (1600 μsec) the ON period of the first impedance calculation mode (135 μsec), for each time the first port 24 is switched to ON. Then, the electric potentials VS1ON and the VS2ON are detected when the 1600 μsec period has elapsed after the first port 24 is switched to ON.

As explained above, in the system of the embodiment, in the first impedance calculation mode, it is possible to detect the element impedance Rs while applying the sweep voltage that rises rapidly with the short time constant τ1 to the oxygen sensor 10. Further, in the second impedance calculation mode, it is possible to detect the element impedance Rs while applying the sweep voltage that rises slowly with the long time constant τ2 to the oxygen sensor 10. In other words, with the system of the embodiment, in the first impedance calculation mode, the element impedance Rs for the high frequency input can be detected as Rs1, and in the second impedance calculation mode, the element impedance Rs for the low frequency input can be detected as Rs2.

[Deterioration Determination Using the Impedance Ratio Rs1/Rs2]

Figure 5:
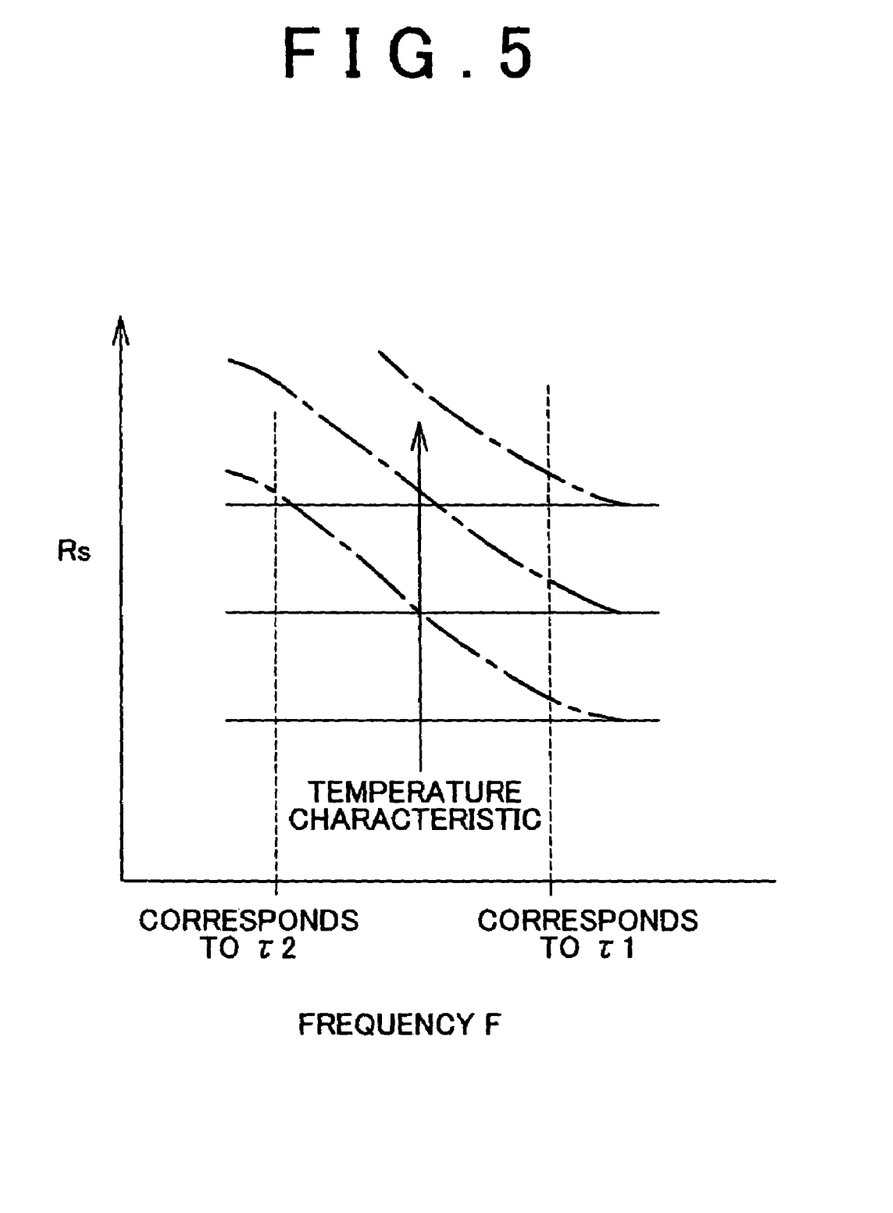
FIG. 5 is an explanatory figure of characteristics of element impedance of an oxygen sensor.

FIG. 5 is an explanatory figure of characteristics of the element impedance Rs of the oxygen sensor 10. The solid characteristic lines in FIG. 5 show the relationship of the element impedance Rs of the normally operating oxygen sensor 10 and the input frequency. Each one of the plurality of these characteristic lines shows the characteristics exhibited at different temperatures. As shown by the characteristic lines, the element impedance Rs exhibits substantial change in response to change of the temperature of the oxygen sensor 10. Accordingly, it is not possible to determine whether the oxygen sensor 10 is functioning normally based on detection of the element impedance Rs alone.

The long dashed short dashed characteristic lines show the relationship of the element impedance Rs of the deteriorated oxygen sensor 10 and the input frequency. As shown by these characteristic lines, the element impedance Rs of the deteriorated oxygen sensor 10 exhibits frequency characteristics. These frequency characteristics are not generated when the oxygen sensor 10 is functioning normally. Accordingly, if the element impedance exhibits frequency characteristics, it is possible to determine that the oxygen sensor 10 is subject to deterioration.

Figure 6:
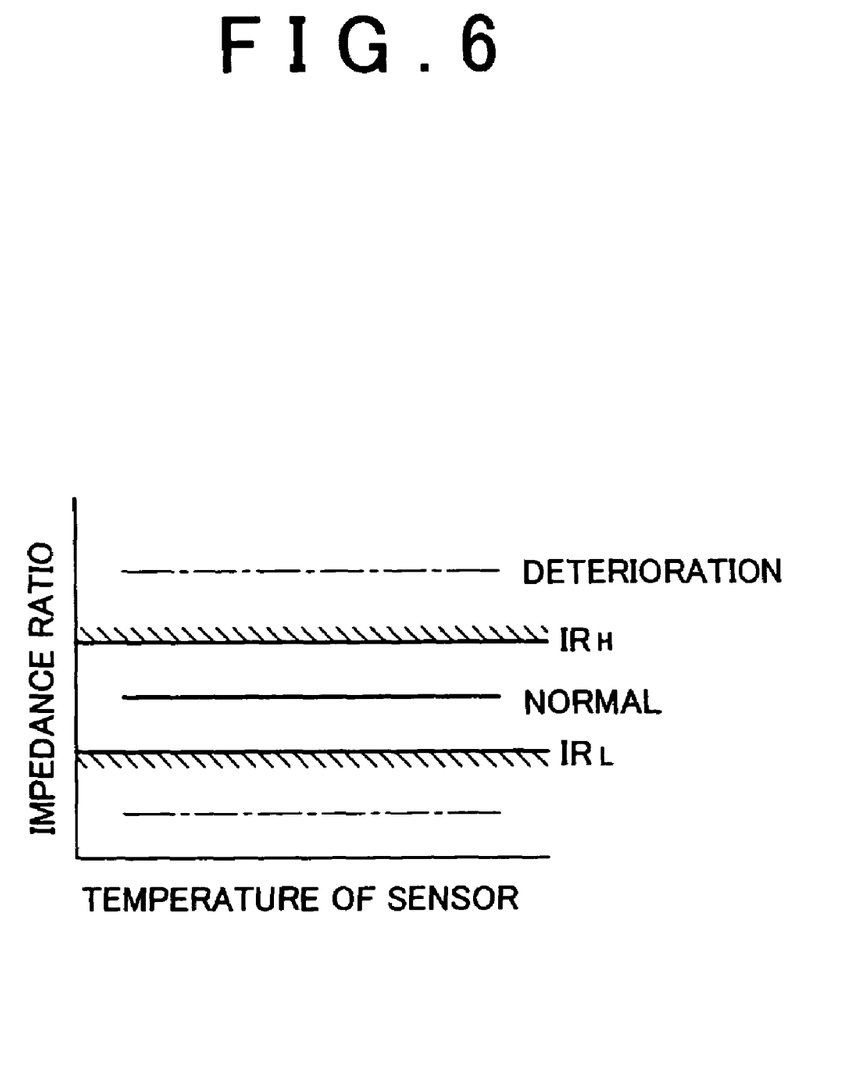
FIG. 6 shows a relationship of normal and deteriorated determination regions and a temperature of the oxygen sensor, based upon an impedance ratio.

As described previously, the ECU 20 executes the deterioration determination (refer to step S108) for the oxygen sensor 10 based on whether the impedance ratio Rs1/Rs2 is larger than the lower limit determination value $IR_L$ (for example, 0.8), and smaller than the upper limit determination value $IR_H$ (for example, 1.2). As shown in FIG. 5, the element impedance Rs of the deteriorated oxygen sensor 10 exhibits frequency characteristics regardless of the temperature of the oxygen sensor 10. As a result, it is possible to accurately execute determination of whether the element impedance Rs is exhibiting frequency characteristics using a substantially constant reference, regardless of the temperature of the oxygen sensor 10. In other words, as shown in FIG. 6, it is possible to constantly and precisely determine whether the oxygen sensor 10 is functioning normally or has deteriorated based on the fixed determinations values $IR_L$ and $IR_H$, regardless of the temperature of the oxygen sensor 10. Thus, with the system of the embodiment it is possible to constantly and precisely execute deterioration determination for the oxygen sensor 10.

[Relationship of the Element Impedance Rs and the Time Constants τ1 and τ2]

As described previously, the ECU 20, in the first impedance calculation mode, applies the sweep voltage that changes at the time constant τ1 to the oxygen sensor 10. In this mode, the ECU 20 maintains the first port 24 in the ON position for 135 μsec for each time the first port 24 is switched to ON. In other words, in the first impedance calculation mode, the ECU 10 applies the sweep voltage that changes at the time constant τ1 to the oxygen sensor 10 for a period of 135 μsec for each time the first port 24 is switched to ON.

Moreover, the ECU 10, in the second impedance calculation mode, applies the sweep voltage that changes at the time constant τ2 to the oxygen sensor 10. In this mode, the ECU 20 maintains the first port 24 in the ON position for 1600 μsec, each time the first port 24 is switched to ON. In other words, in the second impedance calculation mode, the ECU 10 applies the sweep voltage that changes at the time constant τ1 to the oxygen sensor 10 for a period of 1600 μsec for each time the first port 24 is switched to ON.

The element impedance Rs, as shown by Equation (2), (τ1=C1/{1/(Rs+R1)+1/R2}), is reflected in the time constant τ1 used in the first impedance calculation mode. According to the relationship, the time constant τ1 becomes a larger value as the element impedance Rs becomes a larger value. Similarly, the time constant τ2 used in the second impedance calculation mode also becomes a larger value as the element impedance becomes a larger value, as shown by Equation (8), (τ2=(C1+C2)/{1/(Rs+R1)+1/R2}).

Hereinafter, an explanation will be given concerning the effects that occur due to the time constants τ (τ1, τ2) of the respective sweep voltages exhibiting the above tendencies with respect to the element impedance Rs, and respectively limiting the periods for which the respective sweep voltages are applied for each time the first port 24 is switched to ON in the first impedance calculation and the second impedance calculation modes.

[Relationship of the Convergence Value of the Current/the Voltage and the Element Impedance Rs]

Figure 7:
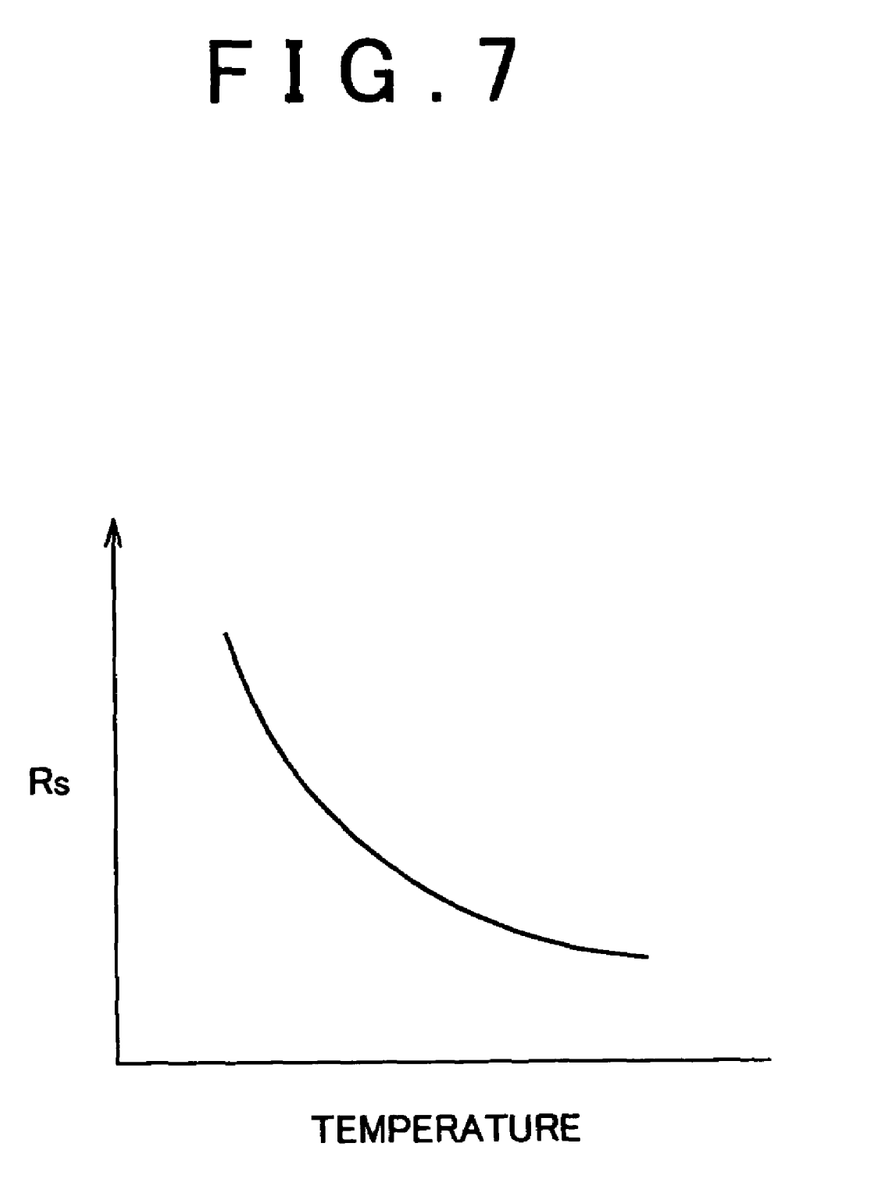
FIG. 7 is an explanatory figure of temperature characteristics of the element impedance of the oxygen sensor.

FIG. 7 shows the temperature characteristics of the element impedance Rs of the oxygen sensor 10. The element impedance Rs, as shown in FIG. 7, becomes a lower value as the temperature of the oxygen sensor 10 increases. When the ECU 20 detects the element impedance Rs, the first port 24 is switched to ON and the sweep voltage is applied to the oxygen sensor 10. At this time, the current I that changes at the time constant τ (time constant τ1 or τ2) flows in the oxygen sensor 10. Further, the current I converges on a value expressed by Equation (9) below if the sweep voltage is applied for a sufficiently long period of time.

$$\text{Convergence Value of the Current } I = 5/(R2+R1+Rs) \quad (9)$$

As is clearly apparent from Equation (9), a convergence value of the current I flowing in the oxygen sensor 10 when detecting the element impedance Rs is a value that becomes smaller as the element impedance Rs becomes larger. On the other hand, the convergence value becomes larger as the element impedance Rs becomes smaller. Accordingly, the circuit configuration within the ECU 20 is such that as the temperature of the oxygen sensor 10 becomes higher (the element impedance Rs becomes smaller), it is easier for the flow of the current I in the oxygen sensor 10 to increase; on the other hand, as the temperature of the oxygen sensor 10 becomes lower (the element impedance Rs becomes larger), the flow of the current I in the oxygen sensor 10 is reduced more easily.

It should be noted that, in the ECU 20, the convergence value of the sweep voltage applied to the oxygen sensor 10 when detecting the element impedance Rs is equal to a convergence value of the electric potential VS2 of the second sampling point 50. In addition, the convergence value of the electric potential VS2 can be expressed using Equation (10) below.

$$\text{Convergence Value of the } VS2 = 5 \cdot Rs/(R2+R1+Rs) \quad (10)$$
$$= 5/[\{(R2+R1)/Rs\}+1]$$

As is clearly apparent from Equation (10), the convergence value VS2 is a value that becomes larger as the element impedance Rs becomes larger. On the other hand, the convergence value VS2 becomes smaller as the element impedance Rs becomes smaller. Accordingly, the circuit configuration within the ECU 20 is such that as the temperature of the oxygen sensor 10 becomes higher (Rs becomes smaller), the voltage applied to the oxygen sensor 10 is reduced so as to be small; on the other hand, as the temperature of the oxygen sensor 10 becomes lower (Rs becomes larger), it becomes easier for a high voltage to be applied to the oxygen sensor 10.

[Relationship of the Sweep Voltage Application Period and the Voltage/the Current]

As described previously, in the system of the embodiment, as the element impedance Rs becomes smaller, the time constant τ (time constant τ1 or τ2) of the sweep voltage becomes a smaller value. In other words, the sweep voltage applied to the oxygen sensor 10 reaches the convergence value more quickly as the element impedance Rs becomes smaller.

In the embodiment, the application period (135 μsec) for the sweep voltage used in the first impedance calculation mode, and the application period (1600 μsec) for the sweep voltage used in the second impedance calculation mode are determined while taking the above described characteristics as presuppositions. More specifically, the respective application periods are set by taking as a reference the time required for the sweep voltage to substantially reach the convergence voltage in the respective modes, when the oxygen sensor 10 exhibits the smallest element impedance Rs during actual use.

Accordingly, in the ECU 20, in whichever of the modes, in the case that the temperature of the oxygen sensor 10 has increased sufficiently (the element impedance Rs is small), the sweep voltage reaches the convergence value shown by Equation (10), and the current I that flows in the oxygen sensor 10 reaches the convergence value shown in Equation (9), during the application period of the sweep voltage. In contrast to this, in the case that the temperature of the oxygen sensor 10 has not increased sufficiently (the element impedance Rs is large), in whichever of the modes, a situation occurs in which the application period of the sweep voltage is interrupted prior to when the sweep voltage or the flowing current I reach their respective convergence values.

[Phenomena when the Element Impedance Rs is Small]

The above described information can be systematized in the following manner. First, in the case that the temperature of the oxygen sensor 10 has increased sufficiently and the element impedance Rs is sufficiently small, the phenomena that occurs within the ECU 20 can be systematized as follows.

(B1) Each time the first port 24 is switched to ON, the sweep voltage that reaches the convergence value is applied to the oxygen sensor 10, and the current I that reaches the convergence value flows in the oxygen sensor 10. (B2) The convergence value of the current I becomes a comparatively large value. (B3) The convergence value of the sweep voltage is reduced to a small value.

Even when the convergence value of the current I is a comparatively large value, if the convergence value of the sweep voltage is reduced to a small value, the electric power supplied to the oxygen sensor 10 can be restricted to a suitable value. Thus, with the system of the embodiment it is possible to reliably inhibit excessive supply of the electric power to the oxygen sensor 10 when detection processing of the element impedance Rs is executed under conditions in which the temperature of the oxygen sensor 10 has increased sufficiently (namely, under conditions in which the element impedance Rs is sufficiently small).

[Phenomena when the Element Impedance Rs is Large]

Next, when the temperature of the oxygen sensor 10 has not increased sufficiently, and the element impedance Rs is a large value, the phenomena that occurs within the ECU 20 can be systematized in the following manner.

(C1) The convergence value of the current I becomes a comparatively small value. (C2) The convergence value of the sweep voltage becomes a comparatively large value. (C3) The individual application periods for the respective sweep voltages are terminated during the process of the respective rises, prior to the respective sweep voltages reaching their convergence values.

Even if the sweep voltage converges on a comparatively large value, it is possible to inhibit the amount of the electric power supplied to the oxygen sensor 10 to a suitable value, if the convergence value of the current I is reduced to a small value. Further, even if the convergence value of the sweep voltage is a large value, if the application period is terminated prior to the sweep voltage reaching the convergence value, the voltage actually applied to the oxygen sensor 10 can be reduced to a sufficiently small value. Accordingly, with the system of the embodiment, even under conditions in which the temperature of the oxygen sensor 10 has not increased sufficiently, (namely, under conditions in which the element impedance Rs is a comparatively large value), it is possible, along with the detection processing of the element impedance Rs, to reliably inhibit excessive supply of the electric power to the oxygen sensor 10.

It should be noted that in the embodiment of the invention the first switching device 22, the second resistor 26, the first resistor 30, the first condenser 31, and the second condenser 46 may be regarded as corresponding to a "sweep voltage application element" and a "sweep constant switching device".

Further, a "sensor current detection device" may be regarded as being realized by the ECU 20 detecting the electric potential VS1 of the first sampling point 28 and the electric potential VS2 of the second sampling point 50 (refer to Equation (5)). In addition, an "element impedance calculation device" may be regarded as being realized by the ECU 20 calculating the element impedance Rs in accordance with Equation (7).

Moreover, in the embodiment described above, the first switching device 22, the second resister 26, the first resistor 30 and the oxygen sensor 10 itself may be regarded as corresponding to a "sweep voltage convergence value changing device".

Further, in the embodiment described above, the first switching device 22 connected to the power source voltage may be regarded as corresponding to a "constant voltage generation device", and the second resistor 26 and the first resistor 30 may be regarded as corresponding to a "resistor".

Moreover, in the embodiment described above, the 135 μsec utilized in the first impedance calculation mode and the 1600 μsec utilized in the second impedance calculation mode may be regarded as corresponding to "predetermined application period".

Further, in the respective modes, a "sweep voltage application interruption device" may be regarded as being realized by the ECU 20 switching the first port 24 to OFF along with termination of the application period.

Moreover, in the embodiment described above, the first condenser 31 and the second condenser 46 may be regarded as corresponding to a "condenser".

In addition, in the embodiment described above, a "time constant switching device" may be regarded as being realized by the ECU 20 switching the second port 44 between ON and OFF; an "element impedance calculation device" may be regarded as being realized by the ECU 20 calculating the first impedance Rs1 and the second impedance Rs2; an "element impedance ratio calculation device" may be regarded as being realized by the ECU 20 executing the processing of step S106; and a "deterioration diagnosis device" may be regarded as being realized by the ECU 20 executing the processing of step S108.

Further, in the embodiment described above, the first switching device 22 connected to the power source voltage may be regarded as corresponding to a "constant voltage generation device"; and the first condenser 31, the second condenser 46, and the second switching device 42 may be regarded as corresponding to a "variable capacity condenser". Moreover, a "capacity changing device" may be regarded as being realized by the ECU 20 switching the second port 44 between ON and OFF.

The invention, as configured above, allows the following effects to be obtained.

At the same time as applying the sweep voltage to the oxygen sensor, it is possible to calculate the element impedance based on the current flowing in the oxygen sensor when the sweep voltage is being applied. In addition, as the element impedance becomes larger, the time constant of the sweep voltage is set to increase such that the rise of the sweep voltage is more gradual. Accordingly, it is easily possible to inhibit excessive voltage from being applied to both terminals of the oxygen sensor when the element impedance is large.

Further, as the element impedance becomes larger, it is possible to set the convergence value of the sweep voltage applied to the oxygen sensor to become smaller. Accordingly, when the element impedance is small, and a large current flows in the oxygen sensor, it is possible to effectively inhibit the supply of the electric power to the oxygen sensor from becoming excessive by setting the applied voltage (the sweep voltage) to a small value.

In addition, by arranging the power source generating the constant voltage, the resistor, and the oxygen sensor in series, it is possible to easily realize a function that makes the convergence value of the sweep voltage smaller as the element impedance of the oxygen sensor becomes smaller.

Moreover, it is possible to interrupt application of the sweep voltage at the time point when the period necessary for the sweep voltage for the element impedance to converge on the convergence value has elapsed when the oxygen sensor is operating under normal usage conditions. As a result, when the element impedance is large, the sweep voltage is interrupted prior to when the sweep voltage reaches the convergence value, and thus it is possible to inhibit the electric power supplied to the oxygen sensor from becoming excessive.

In addition, a RC circuit is configured by the oxygen sensor itself and the condenser connected in parallel with it. Moreover, it is possible to supply constant voltage to the RC circuit during the application period of the sweep voltage. Given this, it is possible to satisfy the requirement that the time constant is set to increase as the element impedance becomes larger due to the characteristics of the RC circuit.

Further, it is possible to apply the sweep voltage using, at the least, two of the time constant for the single element impedance. Moreover, it is possible to execute the deterioration diagnosis for the oxygen sensor based on the ratio of the element impedances calculated with respect to each of the time constants. By adopting this method, it is possible to precisely execute deterioration detection for the oxygen sensor without the temperature characteristics of the element impedance having any affect. Moreover, it is possible to easily switch the time constant of the sweep voltage by changing the capacity of the condenser connected in parallel with the oxygen sensor.

What is claimed is:

1. An element impedance detection apparatus for an oxygen sensor, comprising:
   a sweep voltage application device that applies a sweep voltage to the oxygen sensor;
   a sensor current detection device that detects a sensor current flowing in the oxygen sensor accompanying application of the sweep voltage;
   an element impedance calculation device that calculates an element impedance of the oxygen sensor, based on the sweep voltage and the sensor current; and
   a sweep time constant changing device that increases a time constant of the sweep voltage as the element impedance becomes larger.

2. The element impedance detection apparatus according to claim 1, wherein the sweep voltage application device includes a sweep voltage convergence value changing device that sets a convergence value of the sweep voltage to become smaller as the element impedance becomes larger.

3. The element impedance detection apparatus according to claim 2, wherein the sweep voltage application device includes a constant voltage generation device that generates a constant voltage when connected in series with the oxygen sensor, and a resistor that is arranged between the oxygen sensor and the constant voltage generation device; and
   the sweep voltage convergence value changing device includes the oxygen sensor itself and the resistor.

4. The element impedance detection apparatus according to claim 1, further comprising, a sweep voltage application interruption device that interrupts application of the sweep voltage at a time point when a predetermined application period has elapsed after application of the sweep voltage to the oxygen sensor starts, wherein the predetermined application period is set to a period that is necessary for the sweep voltage for the element impedance to converge on a convergence value when the oxygen sensor is being operated under normal conditions.

5. The element impedance detection apparatus according to claim 1, wherein the sweep voltage application device includes a constant voltage generation device that generates a constant voltage when connected in series with the oxygen sensor, and a condenser which is connected in series with the constant voltage generation device and which is connected in parallel with the oxygen sensor; and
   the sweep time constant changing device changes the time constant in accordance with a capacity of the condenser.

6. The element impedance detection apparatus according to claim 1, wherein the sweep voltage application device includes a time constant switching device that switches the time constant for the single element impedance between, at the least, two of the time constants; and
   the element impedance calculation device includes an element impedance ratio calculation device which calculates the element impedance of the oxygen sensor with respect to, at the least, two of the time constant, and which derives a ratio of the element impedances calculated with respect to each of, at the least, two of the time constant; and a deterioration diagnosis device that executes deterioration diagnosis for the oxygen sensor based on the element impedance ratio.

7. The element impedance detection apparatus according to claim 6, wherein the sweep voltage application device includes a constant voltage generation device which generates a constant voltage when connected in series with the oxygen sensor, and a variable capacity condenser which is connected in series with the constant voltage generation device and which is connected in parallel with the oxygen sensor; and
   the time constant switching device includes a capacity changing device that changes a capacity of the variable capacity condenser.

8. An element impedance detection apparatus for an oxygen sensor, comprising:
   sweep voltage application means that applies a sweep voltage to the oxygen sensor;
   sensor current detection means that detects a sensor current flowing in the oxygen sensor accompanying application of the sweep voltage;
   element impedance calculation means that calculates an element impedance of the oxygen sensor, based on the sweep voltage and the sensor current; and
   sweep time constant changing means that increases a time constant of the sweep voltage as the element impedance becomes larger.

9. An element impedance detection method for an oxygen sensor, comprising the steps of:
   applying a sweep voltage to the oxygen sensor in accordance with a time constant of the sweep voltage;
   detecting a sensor current flowing in the oxygen sensor accompanying application of the sweep voltage;
   calculating an element impedance of the oxygen sensor based on the sweep voltage and the sensor current; and
   changing the time constant such that the time constant of the sweep voltage increases as the element impedance becomes larger.

10. The element impedance detection method according to claim 9, wherein the step of applying the sweep voltage includes the step of changing a convergence value of the sweep voltage such that the convergence value becomes smaller as the element impedance becomes larger.

11. The element impedance detection method according to claim 9, further comprising the step of, interrupting application of the sweep voltage at a time point when a predetermined application period has elapsed after application of the sweep voltage to the oxygen sensor starts, wherein the predetermined application period is set to a period that is necessary for the sweep voltage for the element impedance to converge on a convergence value when the oxygen sensor is being operated under normal conditions.

12. The element impedance detection method according to claim 9, wherein the step of applying the sweep voltage includes the step of changing the time constant for the single element impedance between, at the least, two of the time constant; and
   the step of calculating the element impedance includes the step of deriving a ratio of the element impedances calculated with respect to each of, at the least, two of the time constant by calculating the respective element impedances of the oxygen sensor with respect to, at the least, two of the time constants; and the step of executing deterioration diagnosis for the oxygen sensor based on the element impedance ratio.

* * * * *